| United States Patent [19] | [11] 3,957,578 |
| --- | --- |
| Narita et al. | [45] May 18, 1976 |

[54] METHOD FOR MANUFACTURE OF α-GALACTOSIDASE BY MICROORGANISM

[75] Inventors: Shigeyoshi Narita, Kitami; Hirosuke Naganishi, Hiroshima; Akiyoshi Yokouchi; Ichiro Kagaya, both of Kitami, all of Japan

[73] Assignee: Hokkaido Sugar Co., Ltd., Tokyo, Japan

[22] Filed: Jan. 3, 1975

[21] Appl. No.: 538,468

[52] U.S. Cl. .................................. 195/11; 195/31 R; 195/65; 195/114
[51] Int. Cl.² ........................ C12D 13/10; C13J 1/00; C12D 13/02
[58] Field of Search .................. 195/81, 11, 7, 31 R, 195/62, 66 R, 65, 114

[56] References Cited
UNITED STATES PATENTS

| 3,832,284 | 8/1974 | Suzuki et al. | 195/11 |
| 3,836,432 | 9/1974 | Shimizu et al. | 195/11 |
| 3,867,256 | 2/1975 | Narita et al. | 195/11 |

*Primary Examiner*—A. Louis Monacell
*Assistant Examiner*—Thomas G. Wiseman
*Attorney, Agent, or Firm*—Oblon, Fisher, Spivak, McClelland & Maier

[57] ABSTRACT

When novel mold strains belonging to genus *Absidia* are cultured in an inducer-containing medium of the type ordinarily used for the culture of α-galactosidase producing molds, notably high α-galactosidase activity is produced and absolutely no invertase activity is produced in the mycelia. By treating beet molasses or beet juice with these mycelia, the yield of sucrose can easily be enhanced, since raffinose which is a substance impeding the crystallization of sucrose is effectively decomposed and sucrose is allowed to remain intact.

6 Claims, No Drawings

METHOD FOR MANUFACTURE OF α-GALACTOSIDASE BY MICROORGANISM

BACKGROUND OF THE INVENTION

This invention relates to a method for microorganic production of α-galactosidase.

α-galactosidase is known as an enzyme capable of hydrolyzing raffinose into sucrose and galactose. It has successfully been produced commercially from the mold, *Mortierella vinacea* var. raffinoseutilizer (ATCC 20034) (U.S. Pat. No. 3,647,625). It has subsequently been learned that an enzyme having high α-galactosidase activity is produced from the mold belonging to genus Absidia (U.S. Pat. No. 3,832,284). The enzymes have since been used in the beet sugar industry.

In the enzymes obtained by culturing these molds, however, not only α-galactosidase but also invertase is present. When beet juice or beet molasses (hereinafter referred to briefly as "molasses") is treated by use of such enzymes, the raffinose contained in the molasses is decomposed by the α-galactosidase so as to lessen the hindrance to sucrose crystallization by raffinose in the course of beet sugar production and also enhance the yield of sucrose. However, the invertase which is present therein in conjunction with the α-galactosidase has been found to function adversely in that it causes undesired decomposition of sucrose as well. Because it is economically difficult to accomplish separation of this invertase from the enzymes and further because the invertase activity is weak in contrast to the α-galactosidase activity, the decomposition of sucrose by the invertase has heretofore been tolerated as an incurable innate defect. When a large volume of molasses is treated, however, the volume of sucrose decomposed by the invertase increases proportionally to a level too great to be overlooked.

An object of the present invention is to provide a method for the manufacture of an enzyme having notably high α-galactosidase activity and absolutely no invertase activity by use of novel molds belonging to genus Absidia, i.e. *Absidia griseola* (ATCC 20430) and *Absidia griseola* var. iguchii (ATCC20431), (hereinafter referred to collectively as "molds of the invention").

SUMMARY OF THE INVENTION

To accomplish the object described above according to the present invention there is provided a method thereby a novel mold strain of genus Absidia is cultured in a medium comprising carbon sources, nitrogen sources and inorganic salts and incorporating lactose, galactose, melibiose or raffinose as the inducer under conditions adopted usually for the culture of α-galactosidase producing molds. Consequently, α-galactosidase alone is produced to a notably high activity level and absolutely no invertase is produced within the mycelia. When beet molasses is treated with these mycelia, the raffinose contained in the molasses is advantageously hydrolyzed by the α-galactosidase into sucrose and galactose and, at the same time, the sucrose contained from the beginning in the molasses and the sucrose produced in consequence of the hydrolysis of raffinose are not at all hydrolyzed, permitting the yield of sucrose to be increased over the conventional level.

Other objects and other characteristic features of the present invention will become apparent from the following detailed description of the invention.

DETAILED DESCRIPTION OF THE INVENTION

It has heretofore been known that *Mortierella Vinacea* var. raffinoseutilizer (ATCC No. 20034) and several type strains of genus Absidia have ability to produce α-galactosidase. The inventors have made the discovery that strains of genus Circinella are able to produce highly active α-galactosidase (U.S. Pat. application Ser. No. 437,536, now U.S. Pat. No. 3,867,256). The enzymes which are produced by the action of these molds inevitably contain invertase, small as the quantity may be, in addition to the α-galactosidase. When the molasses is treated by use of these enzymes, raffinose is decomposed to increase the yield of sucrose but, at the same time, sucrose to be recovered as the product also undergoes hydrolysis by invertase to some extent. Only because the activity of invertase is weak in contrast to that of α-galactosidase, however, the hydrolysis of sucrose has been tolerated as an incurable innate defect.

The inventors continued a search after molds capable of producing enzymes in which the α-galactosidase activity is high and absolutely no invertase activity exists. They have consequently made the discovery that when novel strains belonging to genus Absidia are cultured under a fixed set of conditions in an inducer-containing medium of the type usually employed for the culture of molds, a notably high level of α-galactosidase activity not attainable by any of the known molds is produced and absolutely no invertase activity is produced in the cultured mycelia. It has heretofore been known that the α-galactosidase activity produced by conventionally known molds of genus Absidia is relatively high but that the invertase activity is inevitably produced as well. In the enzymes which are produced by the molds of the invention, the α-galactosidase activity exists to a notably high level and absolutely no invertase activity exists. Whe the molasses is treated by using such enzymes, only raffinose is hydrolyzed and sucrose is not hydrolyzed at all. Thus, sucrose can be recovered in a yield much higner than the yield obtained by use of enzymes containing invertase. Since the α-galactosidase activity is high, the amount of mycelia to be added for the purpose of treatment is smaller and the handling involved becomes easier. The molds of the invention have been isolated by one of the inventors from soy sauce Koji and established to belong to genus Absidia.

The present strains can be easily differentiated with *Absidia hyalospora*, and *Absidia lichtheimi*, which can both be isolated from "kurone," by the color and height of colony, and color and shape of columellae, and shape, size and color of the sporangiospores. *Absidia lichtheimi* assimilates glycerol and *Absidia hyalospora* sucrose, however, from a carbon source test the present strain was found to assimilate the following: xylose, soluble starch, glucose, galactose, fructose, maltose, lactose, trehalose, mannitol and sorbitol but, rhamnose, fucose, inositol, glycerol and sucrose are not assimilated. From the above findings the present strains can be said to be a new species and therefore, the inventors propose to name them *Absidia griseola* (ATCC No. 20430) and *Absidia griseola* var. igucii (ATCC No. 20431) respectively. The latter is different from the former merely in that it permits assimilation of glycerol and, therefore, is regarded to be a variant of the former.

The two strains were deposited with ATCC on Aug. 28, 1974. Mycologically, they are characterized as follows:

Absidia griseola (ATCC 20430)

On synthetic mucor agar medium, colony is low and dense, stolon is formed with several sporangiophores. Colony is at first white but as sporangia are formed and age, becomes gray to blue gray. Height is up to 3 mm. On potato extract agar with glucose, growth is slight. Sporangiophores branch densely into corymb shape near the tips and are up to 15 $\mu$ in width. Wall is slightly rough and light brown.

Sporangia are pyriform with apophysis present. The size of the sporangia appearing at the tips of the stolons are larger than those appearing at the ends of the branches and measure up to 80 $\mu$. Sporangiowall is easily ruptured.

Columelae are subglobus rarely with small projections on the outer top surface and measure up to 36 $\mu$ in diameter. Wall is smooth and slightly light purplish brown.

Sporangiospores are light yellow with smooth wall, seldom rough, usually globose and occasionally elliptical or oblong and have a diameter of 4–7 $\mu$ and occasionally up to 10$\mu$.

No chlamydospores nor zygospores can be observed.

The present strain can be differentiated from other Abisida strains from the point that it is comparatively flat, short and has dense colonies. However, it can also be distinguished by its physiological characteristics. Good growth can be seen at 40°C. On synthetic media, Vitamin B$_1$ appears essential. For nitrogen source, nitrate is assimilated and for carbon source soluble starch and glucose. However, with lactose, assimilation occurs late but once started, good growth is observed. Sucrose and glycerol are not assimilated.

Absidia grisela var. iguchii (ATCC No. 20431)

On synthetic mucor agar medium, colony is low and dense, stolon is formed with several sporangiophores. Colony is at first white but as sporangia are formed and age, becomes gray to blue gray. Height is up to 3 mm. On potato extract agar with glucose, growth is slight. Sporangiophores branch densely into corymb shape near the tips and are up to 15$\mu$ in width. Wall is slightly rough and light brown.

Sporangia are pyriform with apophysis present. The size of the sporangia appearing at the tips of the stolons are larger than those appearing at the ends of the branches and measure up to 80$\mu$. Sporangiowall is easily ruptured.

Columellae are subglobus rarely with small projections on the outer top surface and measure up to 36$\mu$ in diameter. Wall is smooth and slightly light purplish brown.

Sporangiospores are light yellow with smooth wall, seldom rough, usually globose and occasionally elliptical or oblong and have a diameter of 4–7 82 and occasionally up to 10$\mu$.

No chlamydospores nor zygospores can be observed.

The present strain is flat, short and forms dense colonies. Good growth can be seen at 40°C. On synthetic media, Vitamin B$_1$ appears essential. For nitrogen source, nitrate is assimilated and for carbon source soluble starch and glucose. However, with lactose, assimilation occurs late but once started, good growth is observed. Sucrose is not assimilated, although glycerol is assimilated.

The molds of the invention described above, when cultured in a medium and under conditions heretofore employed usually for the culture of molds capable of producing $\alpha$-galactosidase, produce mycelia which contain the $\alpha$-galactosidase activity decisively higher than has been attainable and absolutely no invertase activity.

Carbon sources usable for this medium are starch, glucose, glycerin, maltose, dextrin, sucrose and invert molasses, for example. Suitable nitrogen sources are, for example, soybean flour, peanut powder, ground cottonseed, corn steep liquor, meat extract, peptone, yeast extract, nitrates and ammonium salts. Inorganic salts usable include, for example, common salt, potassium chloride, magnesium sulfate, manganese sulfate, iron sulfate, phosphates and calcium carbonate. If occasion demands, vitamins may be incorporated in the medium.

As inducers for effective production of $\alpha$-galactosidase in the mycelia, there are used such well-known substances as lactose, raffinose, melibiose and galactose.

The culture of the molds of the invention is carried out aerobically as is usual in the case of culturing molds. Specifically, the molds of this invention are inoculated to the medium described above and subjected to shaken culture or aerobic culture at a temperature of about 30°C for a period of from 40 to 70 hours, with the pH value controlled in the range of 5 to 8.

When the molds of the invention are cultured as described above, the $\alpha$-galactosidase activity is produced to a notably high level and absolutely no invertase activity is produced in the cultured mycelia. The mycelia thus cultured are obtained and preserved in the form of pellets through a known process comprising the steps of separation from the culture broth by filtration, washing with water, centrifual dehydration, drying, etc.

The cells thus obtained in the form of pellets are packed in or added to a vertical reaction vessel or horizontal reaction vessel and the molasses is allowed to flow through the reaction vessel at pH 4 to 6 at a temperature of 30° to 60°C. While the molasses is in contact with the mycelia, the raffinose present in the molasses is hydrolyzed into sucrose and galactose. Because no invertase is contained in the enzyme obtained by the method of this invention, the enzymatic hydrolysis is effected only on raffinose and is not at all effected on sucrose. Thus the present invention permits the yield of sucrose to be enhanced efficiently.

In an experiment, a medium was prepared by dissolving 1.5% of lactose, 0.5% of glucose, 0.6% of $(NH_4)_2SO_4$, 1.0% of corn steep liquor, 0.4% of $KH_2PO_4$, 0.2% of $MgSO_4 \cdot 7H_2O$ and 0.2% of NaCl, adjusting the pH value to 5.5 by addition of NaOH and thereafter incorporating 0.3% of $CaCO_3$. This medium was divided into five portions each of 200 ml and sterilized. To the sterilized portions, spore suspensions of *Absidia griseola* (ATCC No. 20430), *Absidia griseola* var. iguchii (ATCC No. 20431), *Mortierella vinacea* (ATCC No. 20034), *Absidia reflexa van. Tieghem* (IFO No. 5874) and *Circinella muscae* (ATCC No. 20394) were inoculated in amounts each to give $2 \times 10^6$ spores and subjected to shaken culture for 60 hours at 30°C. At the end of the culture, the mycelia were tested for $\alpha$-galactosidase activity and invertase activity. The results were as shown in Table 1.

Table 1

| Kinds of Mold | Dry mycelia (g/100 ml) | α-galactosidase activity | | Invertase activity | |
|---|---|---|---|---|---|
| | | Total act. (unit/ml) | Spec. act. (unit/g on dry basis) | Total act. (unit/ml) | Spec.act. (unit/g on dry basis) |
| Absidia griseola (ATCC 20430) | 1.30 | 188,900 | $1,453\times10^4$ | 0 | 0 |
| Absidia griseola var. iguchii (ATCC 20431) | 1.29 | 233,000 | $1,816\times10^4$ | 0 | 0 |
| Mortierella vinacea (ATCC 20034) | 1.29 | 31,100 | $241\times10^4$ | 237 | 18,360 |
| Absidia reflexa (IFO 5874) | 1.28 | 63,100 | $493\times10^4$ | 104 | 8,121 |
| Circinella muscae (ATCC 20394) | 1.30 | 144,200 | $1,109\times10^4$ | 54 | 4,189 |

The activity of α-galactosidase and that of invertase as indicated in the specification of this invention have been determined by the method described below.

The values of α-galactosidase activity are those determined by adding 1 ml of mycelia suspension under test to a mixture of 0.5 ml of 0.06M melibiose and 0.5 ml of 0.1M phosphate buffer solution (pH 5.2) to permit reaction to ensue at 40°C for two hours, thereafter heating the reaction mixture in a boiling water bath for five minutes to inactivate the enzyme, then adding 1 ml of 1.8% $Ba(OH)_2.8H_2O$ and 1 ml of 2% $ZnSO_4.7H_2O$ to the reaction solution to deprive the solution of protein, centrifuging the resultant mixture and assaying the resultant protein-free supernatant for glucose content by the glucostat method. In consideration of the fact that the amount of glucose liberated from melibiose and the enzyme concentration are in a proportional relationship up to 1,000 μg of glucose, the suspension was diluted in advance so that it would fall in the measuring range satisfying this relationship. The amount of free glucose was multiplied by the number of dilutions. The α-galactosidase activity which liberated 1 μg of glucose under the conditions mentioned above was taken as 1 unit.

The values of invertase activity are those determined by adding 1 ml of mycelia suspension to a mixture of 0.5 ml of 0.06M sucrose and 0.5 ml of 0.1M phosphate buffer solution (pH 5.0) to permit reaction to ensue under the same conditions as employed for the determination of α-galactosidase activity, centrifuging the resultant reaction solution to remove protein therefrom and assaying the protein-free supernatant for invert sugar content by the Somogyi-Nelson method. The invertase activity which produced 1 μg of invert sugar under the conditions mentioned above was taken as 1 unit.

The dry mycelial weight was found by drying at 105°C that amount of mycelia which had been grown in 100 ml of culture medium and thereafter weighing the dried mass of mycelia.

It is clearly seen from Table 1 that in the mycelia obtained by culturing the molds of the invention, the α-galactosidase activity is much higher than the α-galactosidase activity obtained by use of the α-galactosidase-producing molds known heretofore and absolutely no invertase activity is present.

Usually, in order for 80 percent or more of the raffinose present in the molasses to be hydrolyzed within two and a half hours of reaction time, about $300 \times 10^4$ units of α-galactosidase is required for every one gram of raffinose. To give such treatment to 200 g of molasses (Brix 20°) containing 3.92 g of raffinose, for example, there is required $1.176 \times 10^4$ units of α-galactosidase. In the case of Mortierella vinacea (ATCC No. 20034), since the specific activity thereof is $241 \times 10^4$ units as indicated in Table 1, addition of 4.88 g of the mycelia is required. In contrast, the α-galactosidase by Absidia griseola var. iguchii (ATCC No. 20431) of the present invention has a specific activity of $1.816 \times 10^4$ units. Thus, addition of 0.648 g of the mycelia suffices for the same purpose. The difference in the amount of mycelia to be added becomes more conspicuous in proportion as the raffinose content increases. In the treatment of 200 g of molasses (Brix 60°) containing 11.76 g of raffinose, for example, addition of 14,639 g of mycelia is required in the case of Mortierella vinacea (ATCC No. 20034), whereas addition of 1,943 g, a quantity corresponding to one seventh of the preceding quantity, of mycelia is sufficient in the case of Absidia griseola var. iguchii (ATCC No. 20431).

To 100 g each of molasses (containing 2.90 g of raffinose and 19.6 g of sucrose) with pH 5.2, 3.61 g of dry mycelia of Mortierella vinacea (about $870 \times 10^4$ units of α-galactosidase activity and about 51,800 units of invertase activity) and 0.482 g dry mycelia of Absidia griseola var. iguchii (about $870 \times 10^4$ units of α-galactosidase activity and 0 unit of invertase activity) were added and agitated at 50°C for 2.5 hours. At the end of the reaction, the mycelia were separated from the molasses by filtration and the molasses was analyzed for raffinose content and sucrose content by the process comprising the steps of silyl etherification and gas-liquid chromatography. The results were as shown in Table 2.

Table 2

| Kinds of Mold | Sucrose content (g) | Raffinose content (g) | Decomposition of Raffinose (%) |
|---|---|---|---|
| Mortierella vinacea | 20.77 | 0.568 | 80.40 |
| Absidia griseola var. iguchii | 21.18 | 0.572 | 80.27 |

It is seen from Table 2 that the treatment using the molds of the invention provided a substantially theoretical sucrose increase of 1.58 g, whereas the treatment given under the same conditions by using Mortierella vinacea resulted in an increase of only 1.17 g. The difference of 0.41 g between the two quantities mentioned, therefore, apparently represents the amount of sucrose lost because of the hydrolysis by the invertase. The hydrolysis by the invertase does not necessarily occur only on the sucrose formed in consequence of the hydrolysis of raffinose. Nevertheless, calculation shows that an amount of sucrose equivalent to about 26 percent of the inreased sucrose resulting from the hydrolysis of raffinose was subjected to hydrolysis by the invertase. The data just described have been cited solely by way of a typical example. It will readily be seen therefrom that the amount of sucrose hydrolyzed by the invertase reaches a value too large to be ignored as the amount of molasses to be treated or the amount of mycelia to be added increases.

In the culture of the molds of the invention, an organic acid such as, for example, glycolic acid, citric acid, lactic acid, malic acid, fumaric acid, tartaric acid, succinic acid, glutaric acid, malonic acid, maleic acid, pyruvic acid or galacturnoic acid is added to the medium as the substance for promoting the growth of α-galactosidase in an amount corresponding to 0.2–1.0 percent based on the medium. When the molds of the invention are cultured in a medium of this description, α-galactosidase activity alone is enhanced to a notable extent and absolutely no invertase activity is produced. When the resultant mycelia are used in the reaction for the hydrolysis of raffinose, therefore, the amount in which they are added to the reaction system is markedly smaller than would otherwise be required.

As is evident from the foregoing detailed description, since the method of the present invention provides cultured mycelia which have extremely high α-galactosidase activity per unit weight and contain absolutely no invertase, the enzymes obtained thereby are best suited for the treatment of molasses and therefore find extensive utility in the best sugar industry.

Now, preferred embodiments of this invention will be cited hereinbelow, which are solely illustrated of and not limitative in any way of the present invention.

EXAMPLE 1

A medium having a composition of 0.5% of lactose, 0.7% of glucose, 0.1% of $(NH_4)_2SO_4$, 0.4% of $KH_2PO_4$, 0.2% of $MgSO_4.7H_2O$, 0.06% of $(NH_2)_2CO$, 0.2% of NaCl and 1.2% of corn steep liquor was adjusted with $NH_4OH$ to pH 5.5. In a jar fermentor having an inner volume of 20 liters, 15 liters of the medium thus prepared was placed and, with 800 ppm of cocolin added thereto as an antifoam agent, sterilized for 30 minutes under pressure of 1.2 $kg/cm^2$. The medium was then cooled. To the cooled medium, a spore suspension obtained by culturing *Absidia griseola* var. iguchii (ATCC No. 20431) in potato-glucose agar medium at 27.5°C for ten days was inoculated in an amount to give $1 \times 10^5$ spores/cc of medium and cultured at 30°C for 18 hours, with aeration given at the rate of 1/4 v.v.m. and agitation at the rate of 250 rpm. The mycelia thus propagation were used as the seed. A medium having a composition of 1.5% of lactose, 0.5% of glucose, 0.6% of $(NH_4)_2SO_4$, 1.0% of corn steep liquor, 0.4% of $KH_2PO_4$, 0.2% of $MgSO_4.7H_2O$ and 0.2% of NaCl was adjusted to pH 5.5 and 15 liters of the medium was placed in a jar fermentor having an inner volume of 20 liters and, with 1.280 ppm of cocolin added thereto as an antifoam agent, sterilized for 30 minutes under 1.2 $kg/cm^2$. To the medium thus prepared, 500 ml of said seed was inoculated and cultured at 30°C, with aeration given at the rate of ¼ v.v.m. and agitation at the rate of 350 rpm. The culture was stopped at the time at which the sugar content in the medium reached 0.1 percent (as indicated in terms of glucose by Somogyi method) (44 hours of culture). The relation between the culture time and the amount of α-galactosidase formed was as shown in Table 3. The assay of the culture broth revealed total absence of invertase.

Table 3

| Culture Time (hour) | pH | Residual sugar as glucose (g/100 ml) | Dry mycelia (g/100 ml) | α-galactosidase activity | |
|---|---|---|---|---|---|
| | | | | Total act. (unit/ml) | Spec. act. (unit/g on dry basis) |
| 0 | 6.2 | 1.37 | — | 0 | — |
| 16 | 5.4 | — | — | 0 | — |
| 20 | 6.4 | — | — | 37,200 | — |
| 24 | 6.5 | — | — | 84,300 | — |
| 28 | 6.4 | — | — | 109,000 | — |
| 32 | 5.9 | — | — | 155,400 | — |
| 36 | 5.7 | — | — | 226,700 | — |
| 40 | 5.4 | — | — | 250,900 | — |
| 44 | 5.8 | 0.08 | 1.29 | 257,000 | $1,992 \times 10^4$ |

EXAMPLE 2

*Absida griseola* (ATCC No. 20430) was cultured in entirely the same medium under the same conditions as in Exaple 1. The relation between the culture time and the amount of α-galactosidase formed was as shown in Table 4. Assay of the culture broth revealed total absence of invertase.

Table 4

| Culture Time (hour) | pH | Residual sugar as glucose (g/100 ml) | Dry mycelia (g/100 ml) | α-galactosidase activity | |
|---|---|---|---|---|---|
| | | | | Total act. (unit/ml) | Spec.act. (unit/g on drybasis) |
| 0 | 6.2 | 1.38 | — | 0 | — |
| 16 | 5.5 | — | — | 0 | — |
| 20 | 6.3 | — | — | 25,800 | — |
| 24 | 6.6 | — | — | 60,400 | — |
| 28 | 6.5 | — | — | 76,500 | — |
| 32 | 6.0 | — | — | 112,000 | — |
| 36 | 5.7 | — | — | 162,900 | — |
| 40 | 5.6 | — | — | 186,300 | — |
| 44 | 6.0 | 0.09 | 1.30 | 194,600 | $1,497 \times 10^4$ |

EXAMPLE 3

To each of the twelve portions of a basic medium having a composition of 0.5% of glucose, 0.6% of $(NH_4)_2SO_4$, 1.0% of corn steep liquor, 0.4% of $KH_2PO_4$, 0.2% of $MgSO_4.7H_2O$, 0.2% of NaCl and 0.3% of $CaCO_3$, a different one of the twelve sugars indicated in Table 5 was added in an amount corresponding to 1.5%. The medium was prepared by first dissolving the components in the indicated percentages excepting $CaCO_3$, adjusting the resultant mixture to pH 5.5 and thereafter incorporating $CaCO_3$. Portions, 200 ml each in volume, of the medium were dispensed into Sakaguchi flasks having an inner volume of 1 liter and sterilized for 30 minutes under 1.2 kg/cm². Then spore suspensions of *Absidia griseola* (ATCC No. 20430) and *Absidia grisela* var. iguchii (ATCC No. 20431) were inoculated in amounts to give 1 × 10⁶ spores/cc of medium and cultured at 30°C for 60 hours on a reciprocating vibrator operated at an amplitude of 7 cm and a rate of 136 rpm. The results were as shown in Table 5. Assay revealed perfect absence of invertase in all the mycelia on which the 12 different sugars were used.

EXAMPLE 4

A basic medium having a composition of 1.5% of lactose, 0.5% of glucose, 0.6% of $(NH_4)_2SO_4$, 1.0% of corn steep liquor, 0.4% of $KH_2PO_4$, 0.2% of $MgSO_4.7H_2O$ and 0.2% of NaCl was mixed with 0.6% of citric acid as the agent for promoting the formation of α-galactosidase, then adjusted with $NH_4OH$ to pH 5.0 and thereafter combined with 0.2% of $CaCO_3$. Portions, 200 ml each in volume, of the medium were dispensed in Sakaguchi flasks having an inner volume of 1 liter and sterilized for 30 minutes under 1.2 kg/cm². To the media, spore suspensions of *Absidia griseola* (ATCC No. 20430) and *Absidia griseola* var. iguchii (ATCC No. 20431) were inoculated in amounts to give 1 × 10⁶ spores/cc of medium and cultured at 30°C for 60 hours on a reciprocating vibrator operated at an amplitude of 7 cm and a rate of 136 rpm. The results were as shown in Table 6. For comparison, the strains were cultured in a medium identical to the aforementioned medium except for omission of the addition of citric acid under the same conditions and the cultured broths were assayed for α-galactosidase activity. These results are also shown in the table.

Table 5

| Saccharide | *Absidia griseola* ATCC No. | Residual sugar as glucose (g/100 ml) | Dry mycelia (g/100 ml) | α-galactosidase activity Total act. (unit/ml) | Spec. act. (unit/g on dry basis) |
|---|---|---|---|---|---|
| Xylose | 20430 | 0.09 | 1.16 | 0 | 0 |
|  | 20431 | 0.05 | 1.28 | 0 | 0 |
| Arabinose | 20430 | 0.06 | 1.13 | 0 | 0 |
|  | 20431 | 0.05 | 1.19 | 0 | 0 |
| Glucose | 20430 | 0.03 | 1.21 | 0 | 0 |
|  | 20431 | 0.02 | 1.38 | 0 | 0 |
| Fructose | 20430 | 0.02 | 1.21 | 0 | 0 |
|  | 20431 | 0.03 | 1.23 | 0 | 0 |
| Mannose | 20430 | 0.05 | 1.22 | 0 | 0 |
|  | 20431 | 0.04 | 1.32 | 0 | 0 |
| Galactose | 20430 | 0.05 | 1.22 | 52,600 | 431 × 10⁴ |
|  | 20431 | 0.04 | 1.31 | 46,200 | 353 × 10⁴ |
| Maltose | 20430 | 0.05 | 1.18 | 0 | 0 |
|  | 20431 | 0.04 | 1.24 | 0 | 0 |
| Lactose | 20430 | 0.07 | 1.29 | 189,200 | 1,467 × 10⁴ |
|  | 20431 | 0.09 | 1.28 | 234,400 | 1,831 × 10⁴ |
| Melibiose | 20430 | 0.03 | 1.29 | 31,300 | 243 × 10⁴ |
|  | 20431 | 0.03 | 1.30 | 28,600 | 220 × 10⁴ |
| Raffinose | 20430 | 0.02 | 0.81 | 58,600 | 724 × 10⁴ |
|  | 20431 | 0.02 | 0.82 | 48,200 | 594 × 10⁴ |
| Soluble starch | 20430 | 0.08 | 1.14 | 0 | 0 |
|  | 20431 | 0.06 | 1.37 | 0 | 0 |
| Dextrin | 20430 | 0.09 | 1.08 | 0 | 0 |
|  | 20431 | 0.06 | 1.37 | 0 | 0 |

Table 5 clearly indicates that the inducing substances which have heretofore been used for the production of α-galactosidase by the culture of conventional molds are invariably effective in the culture of the molds of the invention and that the effect of lactose is most conspicuous.

Table 6

| Kinds of mold | Citric acid | Dry mycelia (g/100 ml) | α-galactosidase activity Total act. (unit/ml) | Spec. act. (unit/g on dry basis) | Invertase activity Total act. (unit/ml) | Spec. act. (unit/g on dry basis) |
|---|---|---|---|---|---|---|
| *Absidia griseola* (ATCC 20430) | Not added | 1.280 | 177,200 | 1,384×10⁴ | 0 | 0 |
|  | Added | 1.260 | 385,400 | 3,059×10⁴ | 0 | 0 |
| *Absidia griseola* var. iguchii (ATCC 20431) | Not added | 1.290 | 230,900 | 1,790×10⁴ | 0 | 0 |
|  | Added | 1.260 | 496,200 | 3,938×10⁴ | 0 | 0 |

It is seen from Table 6 that addition of citric acid as the agent for promoting the formation of α-galactosidase served to increase the α-galactosidase served to increase the α-galactosidase activity by about 2.2 times and permit absolutely no production of invertase activity.

EXAMPLE 2

To each eleven portions the basic medium of Example 4, a different one of the 11 organic acids indicated in Table 7 and Table 8 was added in an amount corresponding to 0.6% and *Absidia griseola* var. iguchii (ATCC No. 20431) and *Absidia griseola* (ATCC No. 20430) were cultured under the same conditions as in Example 4. The resulting α-galactosidase activities obtained with the former mold were as shown in Table 7 and those obtained with the latter mold were as shown in Table 8.

The tables clearly indicate that the organic acids were as effective in promoting the growth of α-galactosidase as citric acid.

EXAMPLE 6

To aliquots of the basic medium of Example 4, citric acid, lactic acid and glycolic acid were added independently in varying amounts corresponding to 0.2, 0.4, 0.6, 0.8 and 1.0%. Under the same conditions, *Absidia griseola* var. iguchii (ATCC No. 20431) and *Absidia griseola* (ATCC No. 20430) were cultured. The resulting α-galactosidase activities obtained with the former mold were as shown in Table 9 and those obtained with the latter mold were as shown in Table 10.

Table 7

| Organic acid | Residual sugar as glucose (g/100ml) | Dry mycelia (g/100ml) | α-galactosidase activity Total act. (unit/ml) | α-galactosidase activity Spec. act. (unit/g on dry basis) | Invertase activity Total acct. (unit/ml) | Invertase activity Spec. act. (unit/g on dry basis) |
|---|---|---|---|---|---|---|
| Glycolic acid | 0.08 | 1.196 | 504,000 | $4,214 \times 10^4$ | 0 | 0 |
| Lactic acid | 0.07 | 1.276 | 475,900 | $3,730 \times 10^4$ | 0 | 0 |
| Malic acid | 0.04 | 1.175 | 421,500 | $3,587 \times 10^4$ | 0 | 0 |
| Fumaric acid | 0.06 | 1.208 | 380,500 | $3,150 \times 10^4$ | 0 | 0 |
| Tartaric acid | 0.08 | 1.394 | 365,100 | $2,619 \times 10^4$ | 0 | 0 |
| Succinic acid | 0.04 | 1.300 | 310,400 | $2,388 \times 10^4$ | 0 | 0 |
| Glutaric acid | 0.06 | 1.370 | 314,100 | $2,293 \times 10^4$ | 0 | 0 |
| Malonic acid | 0.07 | 1.273 | 291,900 | $2,266 \times 10^4$ | 0 | 0 |
| Maleic acid | 0.02 | 1.194 | 240,500 | $2,014 \times 10^4$ | 0 | 0 |
| Pyruvic acid | 0.06 | 1.325 | 307,665 | $2,322 \times 10^4$ | 0 | 0 |
| Galacturonic acid | 0.07 | 1.350 | 371,200 | $2,749 \times 10^4$ | 0 | 0 |
| Comparative Example (no addition of organic acid) | 0.03 | 1.290 | 230,900 | $1,790 \times 10^4$ | 0 | 0 |

Table 8

| Organic acid | Residual sugar as glucose (g/100ml) | Dry mycelia (g/100ml) | α-galactosidase activity Total act. (unit/ml) | α-galactosidase activity Spec. act. (unit/g on dry basis) | Invertase activity Total acct. (unit/ml) | Invertase activity Spec. act (unit/g on dry basis) |
|---|---|---|---|---|---|---|
| Glycolic acid | 0.05 | 1.202 | 359,300 | $2,989 \times 10^4$ | 0 | 0 |
| Lactic acid | 0.03 | 1.204 | 343,300 | $2,851 \times 10^4$ | 0 | 0 |
| Malic acid | 0.03 | 1.190 | 329,400 | $2,768 \times 10^4$ | 0 | 0 |
| Fumaric acid | 0.07 | 1.203 | 293,100 | $2,436 \times 10^4$ | 0 | 0 |
| Tartaric acid | 0.06 | 1.246 | 267,300 | $2,145 \times 10^4$ | 0 | 0 |
| succinic acid | 0.04 | 1.237 | 227,700 | $1,841 \times 10^4$ | 0 | 0 |
| Glutaric acid | 0.04 | 1.294 | 231,000 | $1,785 \times 10^4$ | 0 | 0 |
| Malonic acid | 0.08 | 1.228 | 215,900 | $1,758 \times 10^4$ | 0 | 0 |
| Maleic acid | 0.07 | 1.260 | 197,100 | $1,564 \times 10^4$ | 0 | 0 |
| Pyruvic acid | 0.05 | 1.260 | 226,200 | $1,795 \times 10^4$ | 0 | 0 |
| Galacturonic acid | 0.06 | 1.223 | 273,600 | $2,237 \times 10^4$ | 0 | 0 |
| Comparative Example (no addition of organic acid) | 0.02 | 1.280 | 177,200 | $1,384 \times 10^4$ | 0 | 0 |

Table 9

| Organic acid | Amount added (%) | Residual sugar as glucose (g/100ml) | Dry mycelia (g/100ml) | α-galactosidase activity Total act. (unit/ml) | α-galactosidase activity Spec. act. unit/g on dry basis | Invertase activity Total act. (unit/ml) | Invertase activity Spec. act. (unit/g on dry basis) |
|---|---|---|---|---|---|---|---|
| Citric acid | 0.2 | 0.02 | 1.255 | 346,100 | $2,758 \times 10^4$ | 0 | 0 |
| | 0.4 | 0.05 | 1.260 | 401,200 | $3,184 \times 10^4$ | 0 | 0 |
| | 0.6 | 0.06 | 1.260 | 496,200 | $3,938 \times 10^4$ | 0 | 0 |
| | 0.8 | 0.08 | 1.270 | 478,700 | $3,769 \times 10^4$ | 0 | 0 |
| | 1.0 | 0.09 | 1.273 | 462,900 | $3,636 \times 10^4$ | 0 | 0 |
| Lactic acid | 0.2 | 0.03 | 1.255 | 312,500 | $2,490 \times 10^4$ | 0 | 0 |
| | 0.4 | 0.06 | 1.258 | 390,600 | $3,105 \times 10^4$ | 0 | 0 |
| | 0.6 | 0.07 | 1.276 | 475,900 | $3,730 \times 10^4$ | 0 | 0 |
| | 0.8 | 0.08 | 1.277 | 469,900 | $3,680 \times 10^4$ | 0 | 0 |
| | 1.0 | 0.09 | 1.275 | 448,400 | $3,517 \times 10^4$ | 0 | 0 |

Table 9-continued

| Organic acid | Amount added (%) | Residual sugar as glucose (g/100ml) | Dry mycelia (g/100ml) | α-galactosidase activity | | Invertase activity | |
|---|---|---|---|---|---|---|---|
| | | | | Total act. (unit/ml) | Spec. act. (unit/g on dry basis) | Total act. (unit/ml) | Spec. act. (unit/g on dry basis) |
| | 0.2 | 0.02 | 1.189 | 320,400 | 2,695×10⁴ | 0 | 0 |
| Glycolic | 0.4 | 0.05 | 1.195 | 406,800 | 3,404×10⁴ | 0 | 0 |
| acid | 0.6 | 0.08 | 1.196 | 504,000 | 4,214×10⁴ | 0 | 0 |
| | 0.8 | 0.09 | 1.190 | 487,900 | 4,100×10⁴ | 0 | 0 |
| | 1.0 | 0.09 | 1.190 | 465,800 | 3,914×10⁴ | 0 | 0 |
| Comparative Example (no addition of organic acid) | | 0.03 | 1.290 | 230,900 | 1,790×10⁴ | 0 | 0 |

Table 10

| Organic acid | Amount added (%) | Residual sugar as glucose (g/100ml) | Dry mycelia (g/100ml) | α-galactosidase activity | | Invertase activity | |
|---|---|---|---|---|---|---|---|
| | | | | Total act. (unit/ml) | Spec. act. (unit/g on dry basis) | Total act. (unit/ml) | Spec. act. (unit/g on dry basis) |
| | 0.2 | 0.03 | 1.226 | 263,000 | 2,145×10⁴ | 0 | 0 |
| Citric | 0.4 | 0.03 | 1.244 | 305,500 | 2,456×10⁴ | 0 | 0 |
| acid | 0.6 | 0.04 | 1.260 | 385,400 | 3,059×10⁴ | 0 | 0 |
| | 0.8 | 0.05 | 1.265 | 380,500 | 3,008×10⁴ | 0 | 0 |
| | 1.0 | 0.08 | 1.265 | 350,200 | 2,768×10⁴ | 0 | 0 |
| | 0.2 | 0.02 | 1.203 | 261,500 | 2,174×10⁴ | 0 | 0 |
| Lactic | 0.4 | 0.02 | 1.204 | 295,600 | 2,455×10⁴ | 0 | 0 |
| acid | 0.6 | 0.03 | 1.204 | 343,300 | 2,851×10⁴ | 0 | 0 |
| | 0.8 | 0.04 | 1.205 | 325,100 | 2,698×10⁴ | 0 | 0 |
| | 1.0 | 0.04 | 1.208 | 300,600 | 2,488×10⁴ | 0 | 0 |
| | 0.2 | 0.02 | 1.200 | 270,400 | 2,253×10⁴ | 0 | 0 |
| Glycolic | 0.4 | 0.03 | 1.202 | 338,400 | 2,815×10⁴ | 0 | 0 |
| acid | 0.6 | 0.05 | 1.202 | 359,300 | 2,989×10⁴ | 0 | 0 |
| | 0.8 | 0.06 | 1.207 | 349,500 | 2,896×10⁴ | 0 | 0 |
| | 1.0 | 0.06 | 1.208 | 325,700 | 2,696×10⁴ | 0 | 0 |
| Comparative Example (no addition of organic acid) | | 0.02 | 1.280 | 177,200 | 1,384×10⁴ | 0 | 0 |

These tables clearly show that the amount of any of the organic acids added as the agent for promoting the production of α-galactosidase was suitable in the range of from 0.2 to 1.0 percent and that the amount of α-galactosidase formed gradually decreased as the amount of the organic acid increased beyond the upper limit of 1.0 percent.

EXAMPLE 7

Beet molasses was diluted with water to 30° Brix and adjusted to pH 5.2 by the addition of sulfuric acid. In 200 g of the resultant solution (containing 5.8 g of raffinose), the mycelia of the mold of the invention (having a dry weight of 0.971 g and 17,640,000 units of α-galactosidase obtained in Example 1 were allowed to react at 50°C for 2 hours 30 minutes while under shaking. At the end of the reaction, the mycelia were separated by filtration and washed with water. The filtrate and the washings were combined. A prescribed volume of this mixture was assayed by paper chromatography for residual raffinose content and increased sucrose content. To be more specific, the specimen was developed in a solvent consisting of 6 parts of n-butanol, 4 parts of pyridine and 3 parts of water. The raffinose zone and the sucrose zone consequently formed were cut off, washed out with water, and assayed by the cysteinecarbazole process. It was found that 81% of the original raffinose content had been decomposed and the sucrose content had been increased by 3.19 g.

EXAMPLE 8

In 200 g of beet molasses of 30° Brix prepared in the same manner as in Example 7, the mycelia of the mold of the invention (having 17,640,000 units of α-galactosidase activity) were allowed to react by the same method as in Example 7. After the reaction, the mycelia were washed with water and the washed mycelia were added to a new supply of diluted molasses and allowed to react. In this manner, the mycelia were used repeatedly in a total of seven treatments. The solution obtained in all the treatments were assayed for residual raffinose content and for increase in sucrose content. The results are shown in Table 11.

Table 11

| Run No. | Increase in sucrose (g) | Decomposition of raffinose(%) | Remaining α-galactosidase activity(%) |
|---|---|---|---|
| 1 | 3.24 | 82.1 | 94 |
| 2 | 3.21 | 82.0 | 92 |
| 3 | 3.17 | 81.0 | 91 |

Table 11-continued

| Run No. | Increase in sucrose (g) | Decomposition of raffinose(%) | Remaining α-galactosidase activity(%) |
|---|---|---|---|
| 4 | 3.05 | 78.0 | 88 |
| 5 | 3.04 | 77.2 | 87 |
| 6 | 3.02 | 77.0 | 86 |
| 7 | 3.01 | 76.8 | 84 |

As is clear from the above Table, the activity of α-galactosidase contained in the mycelia of the mold of the present invention reduced only by 16%, even after being used to treat beet molasses 7 times and the α-galactosidase thus treated can be further used for the decomposition of raffinose.

EXAMPLE 9

Beet molasses was diluted to 50° Brix and then adjusted to pH 5.2 with sulfuric acid. In 200 g of this solution (containing 9.80 g of raffinose), the mycelia of the mold of the invention (having a dry weight of 1.619 g and 29,400,000 units of α-galactosidase activity) obtained in Example 1 were allowed to react at 50°C for 2 hours 30 minutes. At the end of the reaction, the solution thus obtained was assayed for decomposition ratio of raffinose and for increase in sucrose content. The decomposition ratio of raffinose was found to be 60.4 percent and the increase in sucrose content to be 3.99 g respectively.

What is claimed is:

1. A method for the manufacture of α-galactosidase, which comprises culturing a mold *Absidia griseola* (ATCC No. 20430) or *Absidia griseola* var. *iguchii* (ATCC No. 20431) in a culture medium containing substances inductive of α-galactosidase under conditions permitting the formation of α-galactosidase, and recovering the α-galactosidase.

2. A method according to claim 1, wherein the substance inductive of α-galactosidase is at least one member selected from the group consisting of lactose, melibiose, raffinose and galactose.

3. A method according to claim 1, further comprising adding to the culture medium an organic acid selected from the group consisting of citric acid, lactic acid, glycolic acid, fumaric acid, glutaric acid, malic acid, tartaric acid, succinic acid, malonic acid, maleic acid, pyruvic acid and galacturonic acid.

4. A method according to claim 3, wherein the amount of said organic acid to be added to the culture medium is about 0.2–1.0 percent based on said culture medium.

5. A method of reducing the raffinose content of beet juice or beet molasses which comprises adding to said juice or molasses mycelia of the mold *Absidia griseola* (ATCC No. 20430) or *Absidia griseola* var. *iguchii* (ATCC No. 20431) cultured in a culture medium containing a substance inductive of α-galactosidase under conditions permitting the formation of α-galactosidase or the α-galactosidase prepared from said mycelial matter, and keeping the resultant mixture under conditions of enzymatic activity for said α-galactosidase until a portion of said raffinose has been decomposed.

6. A method of claim 5, wherein the substance inductive of α-galactosidase is at least one member selected from the group consisting of lactose, melibiose, raffinose and galactose.

* * * * *